United States Patent
Kawaguchi et al.

(10) Patent No.: US 8,791,065 B2
(45) Date of Patent: Jul. 29, 2014

(54) LOW-CONCENTRATION NUTRITIONAL COMPOSITION

(75) Inventors: Susumu Kawaguchi, Meguro-ku (JP); Yoshifumi Inoue, Nishinomiya (JP)

(73) Assignee: Nutri Co., Ltd., Yokkaichi (JP)

( * ) Notice: Subject to any disclaimer, the term of this patent is extended or adjusted under 35 U.S.C. 154(b) by 28 days.

(21) Appl. No.: 13/141,975

(22) PCT Filed: Oct. 27, 2009

(86) PCT No.: PCT/JP2009/068417
§ 371 (c)(1),
(2), (4) Date: Jun. 23, 2011

(87) PCT Pub. No.: WO2010/082390
PCT Pub. Date: Jul. 22, 2010

(65) Prior Publication Data
US 2011/0257088 A1    Oct. 20, 2011

(30) Foreign Application Priority Data

Jan. 19, 2009 (JP) ................ 2009-009102
Jan. 26, 2009 (JP) ................ 2009-014512

(51) Int. Cl.
*A23L 1/305* (2006.01)
*A23L 1/302* (2006.01)
*A23L 1/304* (2006.01)
*A23L 1/09* (2006.01)

(52) U.S. Cl.
USPC ........................................... 514/5.7

(58) Field of Classification Search
None
See application file for complete search history.

(56) References Cited

U.S. PATENT DOCUMENTS

| 6,248,390 B1 | 6/2001 | Stillman |
| 6,890,571 B2 | 5/2005 | Shi et al. |
| 2009/0011990 A1 | 1/2009 | Bouritius et al. |

FOREIGN PATENT DOCUMENTS

| EP | 1362517 A1 | 11/2003 |
| JP | 2004-051494 | 2/2004 |
| JP | 2004-097119 | 4/2004 |
| WO | 0162108 A1 | 8/2001 |
| WO | 2007004883 A2 | 1/2007 |
| WO | WO 2008/054211 | * 5/2008 |
| WO | WO 2008/136420 A1 | 11/2008 |

OTHER PUBLICATIONS

McGough et al. ("Is supplementation with elemental diet feasible in patients undergoing pelvic radiotherapy?" Clinical Nutrition (2006) 25, 109-116).*
Nutrison Low Energy Multi Fibre downloaded on Jan. 16, 2013 from http://nutriciamedical.be and translated to English by Google translator.*
Sagales ("Tipos de nutrición enteral" JANO Mar. 7-13, 2003. vol. LXIV N.$^{mt;epmubo\ ubxmx}$ 1.466, 694-700.*
Jaypee Brothers Medical Publishers (Recent Advances in Pediatrics, Special vol. 6 Gastroenterology, Hepatology and Nutrition, 2000, p. 121).*
CAS Registry file 16389-88-1, Nov. 16, 1984.*
Chinese language office action dated Dec. 19, 2012, its Japanese language translation and its English language translation issued in corresponding Chinese application 200980152898.1.
Extended European search report dated Jul. 3, 2012 issued in corresponding European application 09838357.3.
English translation of International preliminary report on patentability dated Aug. 16, 2011 for corresponding PCT application PCT/JP2009/068417.

* cited by examiner

*Primary Examiner* — Christina Bradley
(74) *Attorney, Agent, or Firm* — Bingham McCutchen LLP

(57) ABSTRACT

The present invention provides an enteral nutritional composition with which the labor of administering water between meals can be saved. The enteral nutritional composition comprises proteins, carbohydrates and lipids, with the calories per ml of the composition being less than 1 kcal and the moisture content being 30 percent by mass or more.

15 Claims, 1 Drawing Sheet

——— Average score of evaluation by nurses in Hospital 1

— — — Average score of evaluation by nurses in Hospital 2

——— 3-Point line: evaluated as "No Difference"

LOW-CONCENTRATION NUTRITIONAL COMPOSITION

CROSS-REFERENCE TO THE RELATED APPLICATIONS

This application is a national stage of international application No. RCT/JP2009/068417, filed on Oct. 27, 2009 and claims the benefit of priority under 35 USC 119 to Japanese Patent Application No. 2009-009102, filed on Jan. 19, 2009 and Japanese Patent Application No. 2009-014512, filed on Jan. 26, 2009, the entire contents of all of which are incorporated herein by reference.

TECHNICAL FIELD

The present invention relates to a low-concentration nutritional composition.

BACKGROUND ART

Nutrients necessary for human to live are introduced into the body, usually, by food intake from the mouth. For those patients who have difficulty in swallowing foods, those patients with a chronic bowel disease and those patients who have difficulty in taking foods from the mouth because of high age or the like, various commercial fluid diets are used (Non-Patent Document No. 1). These fluid diets are thick (highly concentrated) and prepared at 1 kcal/ml or more. Therefore, administration of such fluid diets alone can not supply the amount of water necessary per day, and it is necessary to administer some water between meals. Administration of water between meals imposes considerable labor on caregivers or nurses.

DISCLOSURE OF THE INVENTION

Problem for Solution by the Invention

It is an object of the present invention to provide an enteral nutritional composition with which the labor of administering water between meals can be saved.

Means to Solve the Problem

The present inventor has solved the above problem by decreasing the concentrations of nutrients and increasing the moisture content in a nutritional composition. The present invention may be summarized as follows.

(1) An enteral nutritional composition comprising proteins, carbohydrates and lipids, wherein the calories per ml of the composition are less than 1 kcal and yet the moisture content is 30 percent by mass or more.
(2) The composition of (1), wherein the calories per ml of the composition are 0.5-0.9 kcal.
(3) The composition of (1) or (2), wherein the moisture content is 30-95 percent by mass.
(4) The composition of any one of (1) to (3), wherein the composition further comprises dietary fibers.
(5) The composition of any one of (1) to (4), wherein the composition further comprises vitamins and/or minerals.
(6) The composition of any one of (1) to (5), wherein the composition is a fluid diet.
(7) The composition of any one of (1) to (6), wherein the composition is in a semi-solid or solid state.
(8) The composition of any one of (1) to (6), wherein the composition is in a liquid state.

Effect of the Invention

By using the nutritional composition of the present invention, it is possible to reduce or even eliminate the labor of administering water between meals to those patients who have difficulty in swallowing foods, those patients who have a chronic bowel disease and those patients who have difficulty in taking food from the mouth because of high age or the like.

The present specification encompasses the contents described in the specifications and/or drawings of Japanese Patent Application Nos. 2009-9102 and 2009-14512 based on which the present patent application claims priority.

BEST MODE FOR CARRYING OUT THE INVENTION

Figure 1:
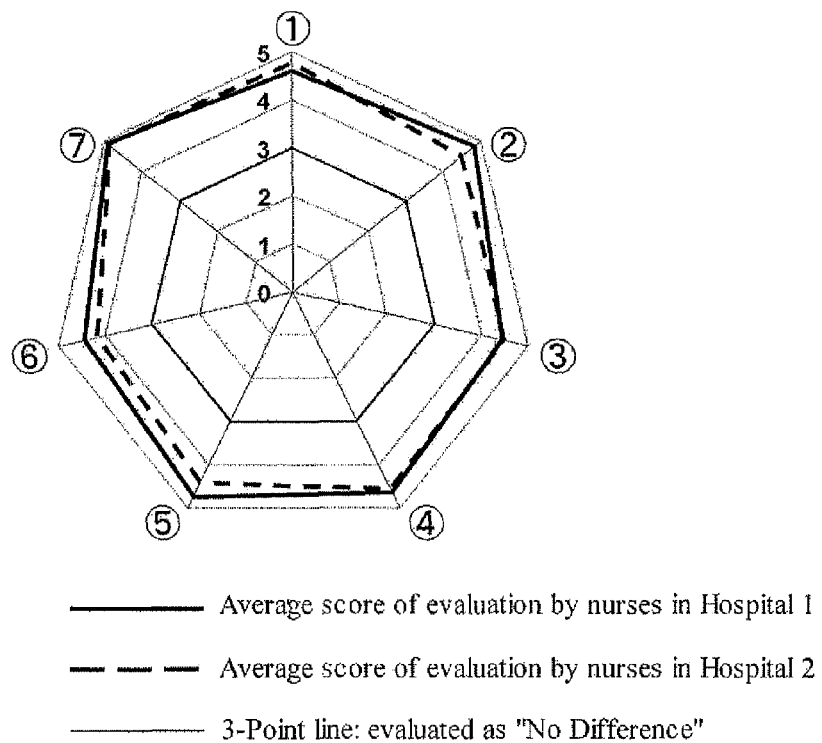
FIG. 1 shows the results of survey by questionnaire on operability test.

Hereinbelow, the present invention will be described in detail.

The present invention provides an enteral nutritional composition comprising proteins, carbohydrates and lipids, wherein the calories per ml of the composition are less than 1 kcal and yet the moisture content is 30 percent by mass or more.

Specific examples of protein components include, but are not limited to, soy protein, collagen degradation products, gelatin, glutamine, arginine, glutamic acid, leucine, isoleucine, valine, threonine, methionine, alanine, lysine, aspartic acid, proline, cysteine, histidine, phenylalanine, tyrosine, tryptophan, asparagine, glycine and serine. The protein content per 100 kcal of the composition is appropriately 1.0-20.0 g, Preferably 1.5-10.0 g, and more preferably 2.0-4.0 g. The amount of protein energy per 100 kcal of the composition is preferably 4.0-80.0 kcal, and more preferably 8.0-16.0 kcal.

Specific examples of protein components include, but are not limited to, detrin, granulated sugar, glucose, maltodextrin, reduced starch degradation products, isomerized sugar syrup, oligosaccharide and lactose. The content per 100 kcal of the composition is appropriately 3.0-30.0 g, preferably 8.0-20.0 g, and more preferably 13.0-17.0 g. The amount of carbohydrate energy per 100 kcal of the composition is appropriately 12.0-120.0 kcal, preferably 32.0-80.0 kcal, and more preferably 52.0-68.0 kcal.

Specific examples of lipids include, but are not limited to, vegetable oils, canola oil, perilla oil, olive oil soybean oil, rapeseed oil and fish oils. The lipid content per 100 kcal of the composition is appropriately 0.2-5.0 g, preferably 1.0-4.0 g, and more preferably 1.5-2.5 g. The amount of lipid energy per 100 kcal of the composition is appropriately 1.8-45.0 kcal, preferably 9.0-36.0 kcal, and more preferably 13.5-22.5 kcal.

The composition of the present invention may further comprise dietary fibers. Specific examples of dietary fibers include, but are not limited to, guar gum degradation products, indigestible dextrin, lactulose and pectin. The dietary fiber content per 100 kcal of the composition is appropriately 0.1-5.0 g, preferably 0.5-3.5 g, and more preferably 0.8-1.5 g.

The composition of the present invention may further comprise vitamins and/or minerals.

Specific examples of vitamins include, but are not limited to, vitamins A, D, $B_1$, $B_2$ and $B_6$, niacin, pantothenic acid, folic acid, vitamins $B_{12}$, C, K and E, biotin and choline bitartrate. The vitamin content per 100 kcal of the composition is appropriately from 0.5 μg to 10.0 g, preferably from 10 μg to 2.0 g, and more preferably from 100.0 μg to 1.0 g.

Specific examples of minerals include, but are not limited to, Na, Cl, K, S, Mg, Ca, P, Fe, I, Mn, Cu, Zn, Sc, Cr, Mo, and dolomite. The mineral content per 100 kcal of the composition is appropriately 200-5000 mg, preferably 500-3000 mg, and more preferably 800-1500 mg.

The composition of the present invention may further comprise cholesterol, lactose, COQ10, flavors, α lipoic acid, EPA, DHA and so on.

The calories per ml of the composition of the present invention are less than 1 kcal. The calories are appropriately 0.5-0.9 kcal, preferably 0.5-0.9 kcal, and more preferably 0.6-0.8 kcal.

The moisture content of the composition of the present invention is 30 percent by mass or more. The moisture content is appropriately 30-95 percent by mass, preferably 30-95 percent by mass, and more preferably 40-90 percent by mass.

The composition of the present invention may be in a liquid, semi-solid (such as gel or paste) or solid state. When the composition is in the state of gel, the firmness of the composition as measured at 25° C. is appropriately 50-10,000 $N/m^2$, preferably 100-5,000 $N/m^2$, and more preferably 500-2,000 $N/m^2$.

For preparing a gel-type composition, a gelatinizing agent such as polysaccharide thickener, agar, gelatin or dextrin may be added to the composition. The amount of the gelatinizing agent to be added to the composition of the present invention may be appropriately determined depending on the desired gel strength.

The composition of the present invention may be prepared by methods well known to those skilled in the art. For example, the composition of the present invention may be prepared as a food product (such as fluid diet) by mixing the above-described components. For preparing a gel-type fluid diet, a gelatinizing agent is dissolved in water and individual components of the composition are mixed therein. Subsequently, the resultant mixture may be packed in a container and cooled. If necessary, the gelatinizing agent may be dissolved in water under heating; the container may be sealed tightly; or the resultant composition may be sterilized by heating.

The composition of the present invention may be used as a fluid diet. Commercial fluid diets are classified into the following three types depending on the foods used therein: natural diet type (in which ordinary foods are used), semi-digested type (in which somewhat degraded foods are used), and digested type (in which foods that can be absorbed without degradation are used). The composition of the present invention is applicable to any of these types of fluid diets. The composition of the present invention is especially effective as a fluid diet for those patients who have difficulty in swallowing foods, those patients who have a chronic bowel disease and those patients who have difficulty in taking food from the mouth because of high age or the like, and is applicable to enteral nutrition.

The composition of the present invention is capable of enteral administration. The dose may be determined in the same manner as the dose of ordinary enteral nutritional composition is determined. For example, when the composition of the present invention is prepared to give 0.5-0.9 kcal per ml, the composition may be administered at a daily dose of about 2400-1400 ml. The dose may be appropriately determined considering the pathology, nutritional status, age, body weight, etc. of the patient.

EXAMPLES

Hereinbelow, the present invention will be described more specifically with reference to the following Examples. These Examples are provided only for illustrating the present invention and should not be construed as limiting the scope of the present invention.

Example 1

Nutritional compositions (Calm Solid 300 and 400) were prepared by the preparation method described below using the raw materials and mixing ratios shown in Table 1 below.
Preparation Method Nutritional compositions were prepared following the steps described below. Dissolving pH adjuster→dissolving gelatinizing agent→dissolving proteins dissolving yeast, vitamins and minerals→emulsifying lipids→adding flavors→homogenizing→packing→sterilizing

TABLE I

| Raw Material | Calm Solid 300 | Calm Solid 400 |
| --- | --- | --- |
| Dextrin | 10.03202531 | 12.65029758 |
| Granulated sugar | 2.623760466 | 3.277029469 |
| Vegetable oils | 1.543388509 | 1.927664394 |
| Casein sodium | 1.929235637 | 2.409580492 |
| Soy protein | 0.964617818 | 1.204790246 |
| Guar gum degradation product | 0.596133812 | 0.74486157 |
| Vitamins/Glucose | 0.108037196 | 0.134936508 |
| Sodium ferrous citrate | 0.003472624 | 0.004337245 |
| Sodium phosphate | 0.289385346 | 0.361437074 |
| Calcium phosphate | 0.054018598 | 0.067468254 |
| KCL | 0.231508276 | 0.289149659 |
| Dry yeast | 0.038063819 | 0.047550059 |
| Dolomite | 0.196782035 | 0.246982 |
| Sodium citrate | 0.210286684 | 0.262644274 |
| Table salt | 0.054018598 | 0.067468254 |
| Gelatinizing agent | 1.556893159 | 1.455989012 |
| Emulsifier | 0.140834201 | 0.175899376 |
| Processed starch | 0.154338851 | 0.14457483 |
| Flavors | 0.135046495 | 0.130117347 |
| Water | 79.13724582 | 74.39579769 |
| | 100 | 100 |

Mixing ratio (%)

By using the nutritional composition of the present invention, it is possible to reduce or even eliminate the labor of administering water between meals to those patients who have difficulty in swallowing foods, those patients who have a chronic bowel disease and those patients who have difficulty in taking foods from the mouth because of high age or the like.

In those patients who have undergone percutaneous endoscopic gastrostomy (PEG), gastroesophageal reflux and diarrhea easily occur. Therefore, it is common practice that water is supplied to them other being gelatinized or mixed with a thickening agent for viscosity adjustment. Alternatively, a commercial jelly for water supply is used. For both methods of water supply, costs are calculated roughly as follows.
[Use of Gelatinizing Agent or Thickening Agent]

When a thickening agent of about ¥5 per gram is used at a daily average of 15 g, economical burden is ¥75/day.

Inclusive of the labor cost for mixing the agent and hygienic control at the time of mixing, the cost is still higher.

[500 ml of Water Supply Using a Commercial Water Supply Jelly]

Economical burden is Isotonic Jelly 100 ml (Nutri Co., Ltd.)×5 units (approx. ¥110/unit)=approx. ¥550.

By using the nutritional composition of the present invention, these costs required for water supply can be reduced.

The method of water supply for patients on PEG is classified roughly into the following four groups: (1) tap water is supplied with a syringe without any processing; (2) tap water is supplied with a syringe after adding thereto a texture improving agent or the like to increase viscosity; (3) a commercial water supply jelly (such as Isotonic Jelly) is used; and (4) transfusion is used. The results of comparison between these four types of methods and the method of using the nutritional composition of the present invention (Calm Solid) are summarized in Table 2.

TABLE 2

|  | Preventive effect against gastro-esophageal reflux | Preventive effect against diarrhea | Labor required for administration | Clean operation is possible | Cost |
|---|---|---|---|---|---|
| (1) Tap water is supplied without any processing | Δ | Δ | ○ | Δ | ⊚ |
| (2) Tap water is supplied after adding thereto a thickening agent to increase viscosity | ○ | ○ | x | Δ | Δ |
| (3) Commercial water supply jelly is supplied | ○ | ○ | ⊚ | ○ | Δ |
| (4) Transfusion is used | ⊚ | ⊚ | Δ | Δ | Δ |
| Calm Solid | ○ | ○ | ⊚ | ⊚ | ○ |

⊚: very suitable
○: suitable
Δ: yes and no
x: not suitable

Test Example 1

1. Purpose of Test

It is a purpose of this test to allow nurses to evaluate the operability of semi-solid fluid diet "Calm Solid" after pouring it into a simple PEG device.

2. Test Method

Consent was obtained from a total of 54 nurses, 34 of them working at a hospital in Hyogo Pref. (hereinafter referred to as "Hospital 1") and 20 working at a hospital in Nara Pref. (hereinafter referred to as "Hospital 2"). Their job experience is shown in Table 3 in terms of the number of years of service. A simple PEG device was created. The nurses were allowed to pour the semi-solid fluid diet "Calm Solid 300 kcal" (prepared in Example 1) into the device and to pursue operations up to flushing. Subsequently, survey by questionnaire was performed with respect to the items shown in Table 4.

The simple PEG device used in the test was a plastic container into which a balloon-type gastric fistula catheter was inserted through a hole provided therein.

During the test, the time required for operations and the weight of Calm Solid before and after administration were measured.

TABLE 3

| Job Experience | Hospital 1 | Hospital 2 | Total |
|---|---|---|---|
| Less than 1 year | 8 nurses | 3 nurses | 11 nurses |
| 1 year to less than 5 years | 16 | 3 | 19 |
| 5 years to less than 10 years | 3 | 7 | 10 |
| 10 years or more | 7 | 7 | 14 |

TABLE 4

Contents of Questionnaire

1. Less concern and labor for water supply.
2. No need to solidify the nutritional composition. So, less time required for operation.
3. Two concentrations of 0.75 ml/kcal and 1.0 ml/kcal are available for the same nutritional composition, making it possible to select finer combinations.
4. Less attention is required for clean operation.
5. Low possibility for mixing of foreign substances.
6. Easy to operate/handle for any one.
7. Less residue in the tube after flushing.

| Evaluation (5-Point Scale) | |
|---|---|
| 5 points | Calm Solid is very good. |
| 4 points | Calm Solid is good. |
| 3 points | No difference. |
| 2 points | Calm Solid is difficult to use. |
| 1 point | Calm Solid is very difficult to use. |

3. Results of Survey by Questionnaire on Operability Test

The results are shown in FIG. 1.

The results revealed that Calm Solid was highly evaluated for any of the items 1 to 7.

The time required for operation is shown in Table 5,

TABLE 5

| | Time required for operation |
|---|---|
| Hospital 1 | 4 min 45 sec |
| Hospital 2 | 3 min 56 sec |
| Total | 4 min 21 sec |

By administering 1 unit of Calm Solid, it is possible to supply about ⅓ of the moisture and nutrients required per day in a short time of around 3 to 5 minutes.

Figure 2:
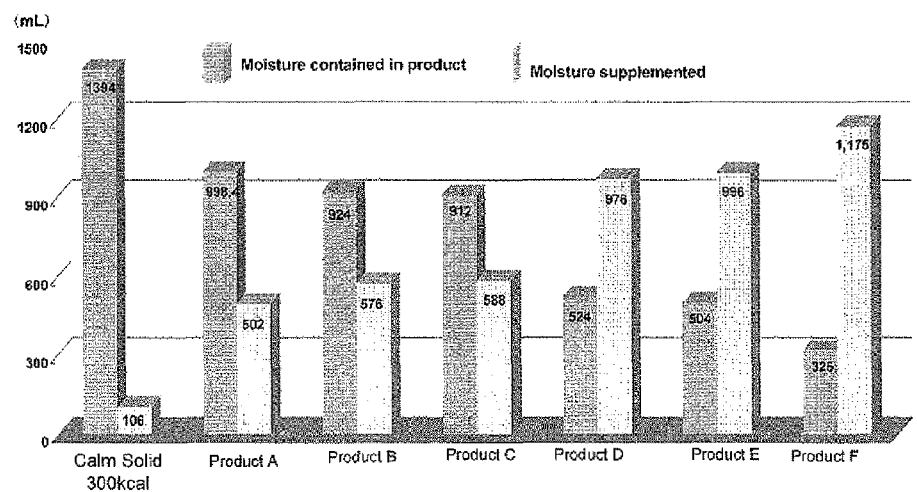
FIG. 2 shows comparison between various products, as administered to give 1,200 kcal, in terms of the moisture content and the moisture supplemented (for the case where a total moisture of 1,500 ml was administered).

FIG. 2 shows comparison with products of other manufacturers, as administered to give 1,200 kcal, in terms of the moisture content and the moisture supplemented (for the case where a total moisture of 1,500 ml was administered).

Compared to the products of other manufacturers, Calm Solid contains more moisture and thus requires less moisture to be supplemented is less. As a result, as shown in the results of the questionnaire survey, less labor is required for operation.

All publications, patents and patent applications cited herein are incorporated herein by reference in their entirety.

Industrial Applicability

The nutritional composition of the present invention is applicable to a fluid diet for those patients who have difficulty in swallowing foods, those patients with a chronic bowel disease and those patients who have difficulty in taking foods from the because of high age or the like.

Prior Art Reference

[Non-Patent Document No. 1]

A Yearbook of Parenteral and Enteral Nutrition 2006, List of Formulations and Instruments, Vol. 5, pp. 37-68, published by JEFF Corporation.

The invention claimed is:

1. An enteral nutritional composition comprising:
dextrin; granulated sugar; vegetable oils; casein sodium; soy protein; guar gum degradation product; vitamins/glucose; sodium ferrous citrate; sodium phosphate; calcium phosphate; KCl: dry yeast; dolomite; sodium citrate; table salt; gelatinizing agent; emulsifier; processed starch; flavors; and water,
wherein the calories per ml of the composition are less than 1 kcal and yet the moisture content is 30 percent by mass or more, and
wherein the composition comprises: a mixing ratio in percent of dextrin, 10.03202531 or 12.65029758; granulated sugar, 2.623760466 or 3.277029469; vegetable oils, 1.543388509 or 1.927664394; casein sodium, 1.929235637 or 2.409580492; soy protein, 0.964617818 or 1.204790246; guar gum degradation product, 0.596133812 or 0.74486157; vitamins/glucose, 0.108037196 or 0.134936508; sodium ferrous citrate, 0.003472624 or 0.004337245; sodium phosphate, 0.289385346 or 0.361437074; calcium phosphate, 0.054018598 or 0.067468254; KCl, 0.231508276 or 0.289149659; dry yeast, 0.038063819 or 0.047550059; dolomite, 0.196782035 or 0.246982; sodium citrate, 0.210286684 or 0.262644274; table salt, 0.054018598 or 0.067468254; gelatinizing agent, 1.556893159 or 1.455989012; emulsifier, 0.140834201 or 0.175899376; processed starch, 0.154338851 or 0.14457483; flavors, 0.135046495 or 0.130117347; and water, 79.13724582 or 74.39579769.

2. The composition of claim 1, wherein the calories per ml of the composition are 0.5-0.9 kcal.

3. The composition of claim 1, wherein the moisture content is 30-95 percent by mass.

4. The composition of claim 1, wherein the composition further comprises dietary fibers.

5. The composition of claim 1, wherein the composition is a fluid diet.

6. The composition of claim 1, wherein the composition is in a semi-solid or solid state.

7. The composition of claim 1, wherein the composition is in a liquid state.

8. The composition of claim 1, wherein the composition comprises: a mixing ratio in percent of dextrin, 10.03202531; granulated sugar, 2.623760466; vegetable oils, 1.543388509; casein sodium, 1.929235637; soy protein, 0.964617818; guar gum degradation product, 0.596133812; vitamins/glucose, 0.108037196; sodium ferrous citrate, 0.003472624; sodium phosphate, 0.289385346; calcium phosphate, 0.054018598KCl, 0.231508276; dry yeast, 0.038063819; dolomite, 0.196782035; sodium citrate, 0.210286684; table salt, 0.054018598; gelatinizing agent, 1.556893159; emulsifier, 0.140834201; processed starch, 0.154338851; flavors, 0.135046495; and water, 79.13724582.

9. The composition of claim 1, wherein the composition comprises: a mixing ratio in percent of dextrin, 12.65029758; granulated sugar, 3.277029469; vegetable oils, 1.927664394; casein sodium, 2.409580492; soy protein, 1.204790246; guar gum degradation product, 0.74486157; vitamins/glucose, 0.134936508; sodium ferrous citrate, 0.004337245; sodium phosphate, 0.361437074; calcium phosphate, 0.067468254; KCl, 0.289149659; dry yeast, 0.047550059; dolomite, 0.246982; sodium citrate, 0.262644274; table salt, 0.067468254; gelatinizing agent, 1.455989012; emulsifier, 0.175899376; processed starch, 0.14457483; flavors, 0.130117347; and water, 74.39579769.

10. A method of applying a low concentration nutritional composition comprising:
performing a percutaneous endoscopic gastrostomy procedure on a subject; and
applying to the subject an enteral nutritional composition, which comprises dextrin; granulated sugar; vegetable oils; casein sodium; soy protein; guar gum degradation product; vitamins/glucose; sodium ferrous citrate; sodium phosphate; calcium phosphate; KCl; dry yeast; dolomite; sodium citrate; table salt; gelatinizing agent; emulsifier; processed starch; flavors; and water,
wherein the calories per ml of the composition are less than 1 kcal and yet the moisture content is 30 percent by mass or more,
wherein the composition comprises: a mixing ratio in percent of dextrin, 10.03202531 or 12.65029758; granulated sugar, 2.623760466 or 3.277029469; vegetable oils, 1.543388509 or 1.927664394; casein sodium, 1.929235637 or 2.409580492; soy protein, 0.964617818 or 1.204790246; guar gum degradation product, 0.596133812 or 0.74486157; vitamins/glucose, 0.108037196 or 0.134936508; sodium ferrous citrate, 0.003472624 or 0.004337245; sodium phosphate, 0.289385346 or 0.361437074; calcium phosphate, 0.054018598 or 0.067468254; KCl, 0.231508276 or 0.289149659; dry yeast, 0.038063819 or 0.047550059; dolomite, 0.196782035 or 0.246982; sodium citrate, 0.210286684 or 0.262644274; table salt, 0.054018598or 0.067468254; gelatinizing agent, 1.556893159 or 1.455989012; emulsifier, 0.140834201 or 0.175899376; processed starch, 0.154338851 or 0.14457483; flavors, 0.135046495 or 0.130117347; and water, 79.13724582 or 74.39579769.

11. The method of claim 10, wherein the composition comprises: a mixing ratio in percent of dextrin, 10.03202531; granulated sugar, 2.623 760466; vegetable oils, 1.543388509; casein sodium, 1.929235637; soy protein, 0.964617818; guar gum degradation product, 0.596133812; vitamins/glucose, 0.108037196; sodium ferrous citrate, 0.003472624; sodium phosphate, 0.289385346; calcium phosphate, 0.054018598; KCl, 0.231508276; dry yeast, 0.038063819; dolomite, 0.196782035; sodium citrate, 0.21 0286684; table salt, 0.0540 18598; gelatinizing agent, 1.556893159; emulsifier, 0.140834201; processed starch, 0.154338851; flavors, 0.135046495; and water, 79.13724582.

12. The method of claim 10, wherein the composition comprises: a mixing ratio in percent of dextrin, 12.65029758; granulated sugar, 3.277029469; vegetable oils, 1.927664394; casein sodium, 2.409580492; soy protein, 1.204790246; guar gum degradation product, 0.74486157; vitamins/glucose, 0.134936508; sodium ferrous citrate, 0.004337245; sodium phosphate, 0.361437074; calcium phosphate, 0.067468254; KCl, 0.289149659; dry yeast, 0.047550059; dolomite, 0.246982; sodium citrate, 0.262644274; table salt, 0.067468254; gelatinizing agent, 1.455989012; emulsifier, 0.175899376; processed starch, 0.14457483; flavors, 0.130117347; and water, 74.39579769.

13. A method comprising:
administering a low-concentration, semi-solid enteral nutritional composition with a high moisture content to a subject who has difficulty taking food from the mouth, wherein the composition includes proteins, carbohydrates and lipids, and the calories per ml of the composition are less than 1 kcal and yet the moisture content is 30 percent by mass or more, and wherein the composition comprises: a mixing ratio in percent of dextrin, 10.03202531 or 12.65029758; granulated sugar, 2.623760466 or 3.277029469; vegetable oils, 1.543388509 or 1.927664394; casein sodium, 1.929235637 or 2.409580492; soy protein, 0.964617818 or 1.204790246; guar gum degradation product, 0.596133812 or 0.74486157; vitamins/glucose, 0.108037196 or 0.134936508; sodium ferrous citrate, 0.003472624 or 0.004337245; sodium phosphate, 0.289385346 or 0.361437074; calcium phosphate, 0.054018598 or 0.067468254; KCl, 0.231508276 or 0.289149659; dry yeast, 0.038063819 or 0.047550059; dolomite, 0.196782035 or 0.246982; sodium citrate, 0.210286684 or 0.262644274; table salt, 0.054018598 or 0.067468254; gelatinizing agent, 1.556893159 or 1.455989012; emulsifier, 0.140834201 or 0.175899376; processed starch, 0.154338851 or 0.14457483; flavors, 0.135046495 or 0.130117347; and water, 79.13724582 or 74.39579769.

14. A method comprising:

administering a low-concentration, semi-solid enteral nutritional composition with a high moisture content to a subject who has difficulty taking food from the mouth, wherein the composition includes proteins, carbohydrates and lipids, and the calories per ml of the composition are less than 1 kcal and yet the moisture content is 30 percent by mass or more, and wherein the composition comprises: a mixing ratio in percent of dextrin, 10.03202531; granulated sugar, 2.623760466; vegetable oils, 1.543388509; casein sodium, 1.929235637; soy protein, 0.964617818; guar gum degradation product, 0.596133812; vitamins/glucose, 0.108037196; sodium ferrous citrate, 0.003472624; sodium phosphate, 0.289385346; calcium phosphate, 0.054018598; KCl, 0.231508276; dry yeast, 0.038063819; dolomite, 0.196782035; sodium citrate, 0.210286684; table salt, 0.054018598; gelatinizing agent, 1.556893159; emulsifier, 0.140834201; processed starch, 0.154338851; flavors, 0.135046495; and water, 79.13724582.

15. A method comprising:

administering a low-concentration, semi-solid enteral nutritional composition with a high moisture content to a subject who has difficulty taking food from the mouth, wherein the composition includes proteins, carbohydrates and lipids, and the calories per ml of the composition are less than 1 kcal and yet the moisture content is 30 percent by mass or more, and wherein the composition comprises: a mixing ratio in percent of dextrin, 12.65029758; granulated sugar, 3.277029469; vegetable oils, 1.927664394; casein sodium, 2.409580492; soy protein, 1.204790246; guar gum degradation product, 0.74486157; vitamins/glucose, 0.134936508; sodium ferrous citrate, 0.004337245; sodium phosphate, 0.361437074; calcium phosphate, 0.067468254; KCl, 0.289149659; dry yeast, 0.047550059; dolomite, 0.246982; sodium citrate, 0.262644274; table salt, 0.067468254; gelatinizing agent, 1.455989012; emulsifier, 0.175899376; processed starch, 0.14457483; flavors, 0.130117347; and water, 74.39579769.

* * * * *